United States Patent
Azhar

(10) Patent No.: US 12,287,473 B2
(45) Date of Patent: Apr. 29, 2025

(54) METHOD AND SYSTEM FOR GENERATING A CHROMATICALLY MODIFIED IMAGE OF COMPONENTS IN A MICROSCOPIC SLIDE

(71) Applicant: Siemens Healthcare Diagnostics Inc., Tarrytown, NY (US)

(72) Inventor: Mohiudeen Azhar, Bangalore (IN)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 350 days.

(21) Appl. No.: 17/756,858

(22) PCT Filed: Dec. 4, 2020

(86) PCT No.: PCT/US2020/063299
§ 371 (c)(1),
(2) Date: Jun. 3, 2022

(87) PCT Pub. No.: WO2021/118881
PCT Pub. Date: Jun. 17, 2021

(65) Prior Publication Data
US 2023/0005185 A1    Jan. 5, 2023

Related U.S. Application Data

(60) Provisional application No. 62/946,056, filed on Dec. 10, 2019.

(51) Int. Cl.
*G02B 21/34* (2006.01)
*G02B 21/00* (2006.01)
(Continued)

(52) U.S. Cl.
CPC ......... *G02B 21/34* (2013.01); *G02B 21/0004* (2013.01); *G02B 21/365* (2013.01);
(Continued)

(58) Field of Classification Search
None
See application file for complete search history.

(56) References Cited

U.S. PATENT DOCUMENTS

2013/0301899 A1* 11/2013 Marcelpoil ............. G06T 7/155
382/133
2017/0176338 A1* 6/2017 Wu ..................... G01N 21/6428

FOREIGN PATENT DOCUMENTS

WO    2015027188 A1    2/2015
WO    2019229556 A1    12/2019

OTHER PUBLICATIONS

International Search Report and Written Opinion of International Application No. PCT/US2020/063299 dated Mar. 11, 2021.
(Continued)

*Primary Examiner* — Delomia L Gilliard

(57) ABSTRACT

A method (400) and a system (200) for generating a chromatically modified image of one or more components on a microscopic slide (303) is disclosed. In one aspect of the invention, the method includes obtaining the image of the one or more components on the microscopic slide (303). Additionally, the method (400) includes processing the image to identify the one or more components. The method (400) further includes segmenting at least one part of the one or more components identified from the image. Furthermore, the method (400) includes chromatically modifying the at least one part of the one or more components and generating a chromatically modified image of the one or more components.

17 Claims, 7 Drawing Sheets

(51) Int. Cl.
  *G02B 21/36* (2006.01)
  *G06T 7/00* (2017.01)
  *G06T 7/11* (2017.01)
  *G06T 7/90* (2017.01)
  *G06V 10/56* (2022.01)
  *G06V 20/69* (2022.01)

(52) U.S. Cl.
  CPC .............. *G06T 7/0012* (2013.01); *G06T 7/11* (2017.01); *G06T 7/90* (2017.01); *G06V 10/56* (2022.01); *G06V 20/695* (2022.01); *G06T 2207/10024* (2013.01); *G06T 2207/10056* (2013.01); *G06T 2207/20036* (2013.01); *G06T 2207/30024* (2013.01)

(56) References Cited

OTHER PUBLICATIONS

Park et al., "Spectroscopic phase microscopy for quantifying hemoglobin concentrations in intact red blood cells", Dec. 1, 2009, Optics Letters, vol. 34, pp. 3668-3670.

Pham et al., "Spectroscopic diffraction phase microscopy" Aug. 15, 2012, Optics Letters, vol. 37, No. 16, pp. 3438-3440.

Sun et al., "Single-shot quantitative phase microscopy based on color-multiplexed Fourier ptychography", Jul. 15, 2018, Optics Letters, vol. 43, No. 14, pp. 3365-3368.

Ou et al., "High numerical aperture Fourier ptychography: principle, implementation and characterization", Feb. 9, 2015, Optics Express, vol. 23, No. 3, pp. 3472-3491.

Gerchberg et al., "A Practical Algorithm for the Determination of the Phase from Image and Diffraction Plane Pictures", 1972, Optik vol. 35, No. 2, pp. 1-6.

Marrison et al., "Ptychography—a label free, high-contrast imaging technique for live cells using quantitative phase Information", 2013, Nature Scientific Reports, vol. 3, No. 2369, pp. 1-7.

\* cited by examiner

METHOD AND SYSTEM FOR GENERATING A CHROMATICALLY MODIFIED IMAGE OF COMPONENTS IN A MICROSCOPIC SLIDE

This application claims priority to U.S. Provisional Application No. 62/946,056, filed on Dec. 10, 2019. The entire content of the above-referenced patent application is hereby expressly incorporated herein by reference.

FIELD OF TECHNOLOGY

The present disclosure relates to the field of spectroscopic analysis of a sample and more particularly to the field of generating a chromatically modified image of components in a microscopic slide.

BACKGROUND

Microscopic staining of cells is a widely used technique to enable efficient visualization of microscopic cells on a slide. Stains emphasize nuclei of white blood cells (WBCs) and therefore enable classification of WBCs into various types. However, staining can have several disadvantages. Variability in the stains and associated techniques, operator variability and significant laboratory costs arising from stain handling are some of the drawbacks associated with the methods existing in the art. As staining is an indispensable process for various biological analyses such as blood smears, clinical pathologists prefer stain based imaging as a clinically approved practice.

Several image processing algorithms have been proposed for standardization of staining techniques. Computational imaging methods such as digital holography microscopy have been proposed as stain-free imaging methods based on use of phase information. Phase contrast microscopy also has been widely used to study samples containing transparent components with varying refractive indices. Optical phase shifts occur primarily due to the thickness and refractive index of the sample. However, it is not easy to decouple the contribution of refractive index from the contribution of phase shift, due to thickness/height of the sample. Traditional microscopic images captured by cameras only contain amplitude information. Therefore, there is no way of obtaining phase information efficiently without appropriate hardware components associated with the microscope. Such computational imaging techniques are also expensive and involve several moving parts which may be prone to damage. Therefore, there exists a need for an efficient way of virtually staining microscopic slides which makes use of phase information associated with the components on the microscopic slide.

SUMMARY

A method of generating a chromatically modified image of one or more components on a microscopic slide is disclosed. In one aspect of the invention, the method includes obtaining the image of the one or more components on the microscopic slide. Additionally, the method includes processing the image to identify the one or more components. The method further includes segmenting at least one part of the one or more components identified from the image. Furthermore, the method includes chromatically modifying the at least one part of the one or more components and generating a chromatically modified image of the one or more components.

In another aspect, a system for generating a chromatically modified image of one or more components on a microscopic slide includes an imaging module. The system further includes one or more processing units, a database coupled to the processing units and a memory coupled to the processing units. The memory includes an image processing module configured for obtaining an image of the illuminated sample. The image processing module is further configured for obtaining the image of the one or more components on the microscopic slide. Additionally, the image processing module is configured for processing the image to identify the one or more components. The image processing module is further configured for segmenting at least one part of the one or more components identified from the image. Furthermore, the image processing module is configured for chromatically modifying the at least one part of the one or more components and generating a chromatically modified image of the one or more components.

In another aspect, a non-transitory computer-readable storage medium having machine readable instructions for generating a chromatically modified image of one or more components on a microscopic slide is disclosed.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present invention is further described hereinafter with reference to illustrated embodiments shown in the accompanying drawings, in which.

DETAILED DESCRIPTION

Figure 1:
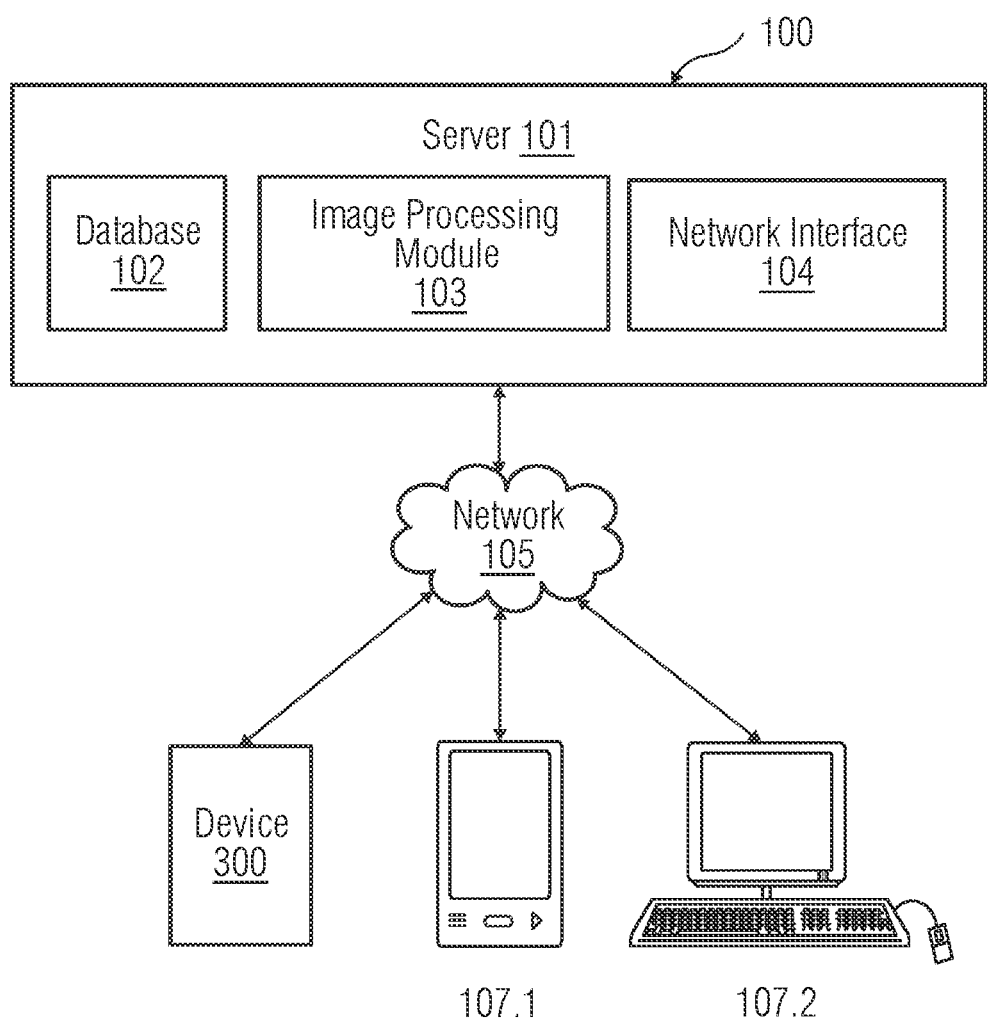
FIG. 1 illustrates block diagram of a client-server architecture which provides geometric modeling of components representing different parts of a real world object, according to an embodiment.

Hereinafter, embodiments for carrying out the present invention are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

FIG. 1 provides an illustration of a block diagram of a client-server architecture that is a geometric modelling of components representing different parts of real-world objects, according to an embodiment. The client-server architecture 100 includes a server 101 and a plurality of client devices 107.1-107.2. Each of the client devices 107.1-107.2 is connected to the server 101 via a network 106, for example, local area network (LAN), wide area network (WAN), WiFi, etc. In one embodiment, the server 101 is deployed in a cloud computing environment. As used herein, "cloud computing environment" refers to a processing environment comprising configurable computing physical and logical resources, for example, networks, servers, storage, applications, services, etc., and data distributed over the network 106, for example, the internet. The cloud computing environment provides on-demand network access to a shared pool of the configurable computing physical and logical resources. The server 101 may include a database 102 that comprises captured images of one or more components on a microscopic slide. The server 101 may include an image processing module 103 that analyzes the image of the one or more components on the microscopic slide. Additionally, the server 101 may include a network interface 104 for communicating with the client devices 107.1-107.2 via the network 105.

The client devices 107.1-107.n include a device 107.1 to generate a chromatically modified image. The device 107.1 may be configured to capture an image of a processed whole blood sample. Such image may be sent to the server 101 via a network interface. The client devices 107.1-107.n also include a user device 107.2, used by a user. In an embodiment, the user device 107.2 may be used by the user, to receive the chromatically modified image of the one or more components on the microscopic slide. The image can be accessed by the user via a graphical user interface of an end user web application on the user device 107.n. In another embodiment, a request may be sent to the server 101 to access the modified image via the network 106. A device 300 may be connected to the server 101 through the network 105. The device 300 may be an imaging module 300 capable of obtaining an image of the one or more components on the microscopic slide. In an embodiment, the imaging module 300 is a Fourier ptychography microscope.

Figure 2:
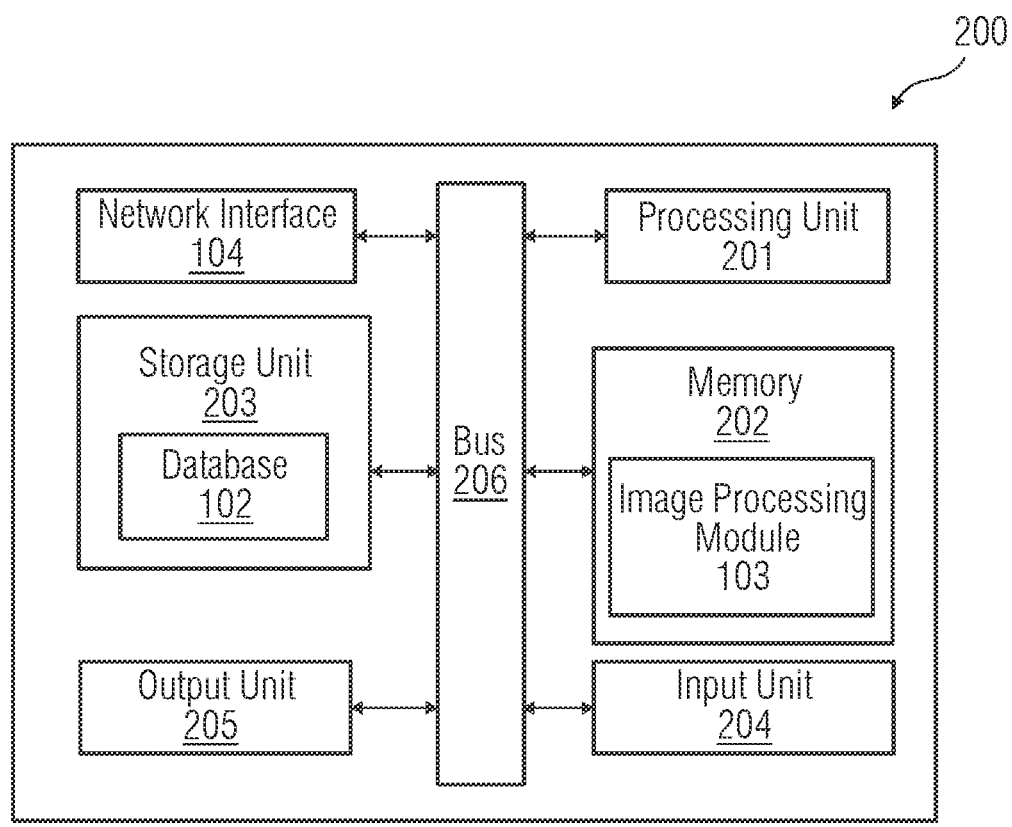
FIG. 2 illustrates a block diagram of a system in which an embodiment of a method of generating a chromatically modified image of one or more components on a microscopic slide can be implemented.

FIG. 2 is a block diagram of a system 101 in which an embodiment can be implemented, for example, as a system to generate a chromatically modified image, configured to perform the processes as described therein. It is appreciated that the server 101 is an exemplary implementation of the system in FIG. 2. In FIG. 2, the system 101 comprises a processing unit 201, a memory 202, a storage unit 203, an input unit 204, an output unit 205 a network interface 104 and a standard interface or bus 206. The system 101 can be a (personal) computer, a workstation, a virtual machine running on host hardware, a microcontroller, or an integrated circuit. As an alternative, the system 101 can be a real or a virtual group of computers (the technical term for a real group of computers is "cluster", the technical term for a virtual group of computers is "cloud").

The processing unit 201, as used herein, means any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 201 may also include embedded controllers, such as generic or programmable logic devices or arrays, application specific integrated circuits, single-chip computers, and the like. In general, a processing unit 201 can comprise hardware elements and software elements. The processing unit 201 can be configured for multithreading, i.e. the processing unit 201 can host different calculation processes at the same time, executing the either in parallel or switching between active and passive calculation processes.

The memory 202 may be volatile memory and non-volatile memory. The memory 202 may be coupled for communication with the processing unit 201. The processing unit 201 may execute instructions and/or code stored in the memory 202. A variety of computer-readable storage media may be stored in and accessed from the memory 202. The memory 202 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 202 includes an image processing module 103 stored in the form of machine-readable instructions on any of the above-mentioned storage media and may be in communication to and executed by processing unit 201. When executed by the processing unit 201, the image processing module 103 causes the processing unit 201 to generate a chromatically modified image of one or more components on a microscopic slide. Method steps executed by the processing unit 201 to achieve the above-mentioned functionality are elaborated upon in detail in FIGS. 4, 5, and 6.

The storage unit 203 may be a non-transitory storage medium which stores a database 102. The database 102 is a repository of images associated with the one or more components on the microscopic slide. The input unit 204 may include input means such as keypad, touch-sensitive display, camera, etc. capable of receiving input signal. The bus 206 acts as interconnect between the processing unit 201, the memory 202, the storage unit 203, the communication interface 107 the input unit 204 and the output unit 205.

Those of ordinary skilled in the art will appreciate that the hardware depicted in FIG. 2 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter, network connectivity devices also may be used in addition or in place of the hardware depicted. The depicted example is provided for the purpose of explanation only and is not meant to imply architectural limitations with respect to the present disclosure.

A system in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through the pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Wash. may be employed if suitably modified. The operating system is modified or created in accordance with the present disclosure as described.

The present invention is not limited to a particular computer system platform, processing unit, operating system, or network. One or more aspects of the present invention may be distributed among one or more computer systems, for example, servers configured to provide one or more services to one or more client computers, or to perform a complete task in a distributed system. For example, one or more aspects of the present invention may be performed on a client-server system that comprises components distributed among one or more server systems that perform multiple functions according to various embodiments. These components comprise, for example, executable, intermediate, or interpreted code, which communicate over a network using a communication protocol. The present invention is not limited to be executable on any particular system or group of systems, and is not limited to any particular distributed architecture, network, or communication protocol.

Disclosed embodiments provide systems and methods for analyzing an image. In particular, the systems and methods may generate a chromatically modified image of one or more components on a microscopic slide.

Figure 3:
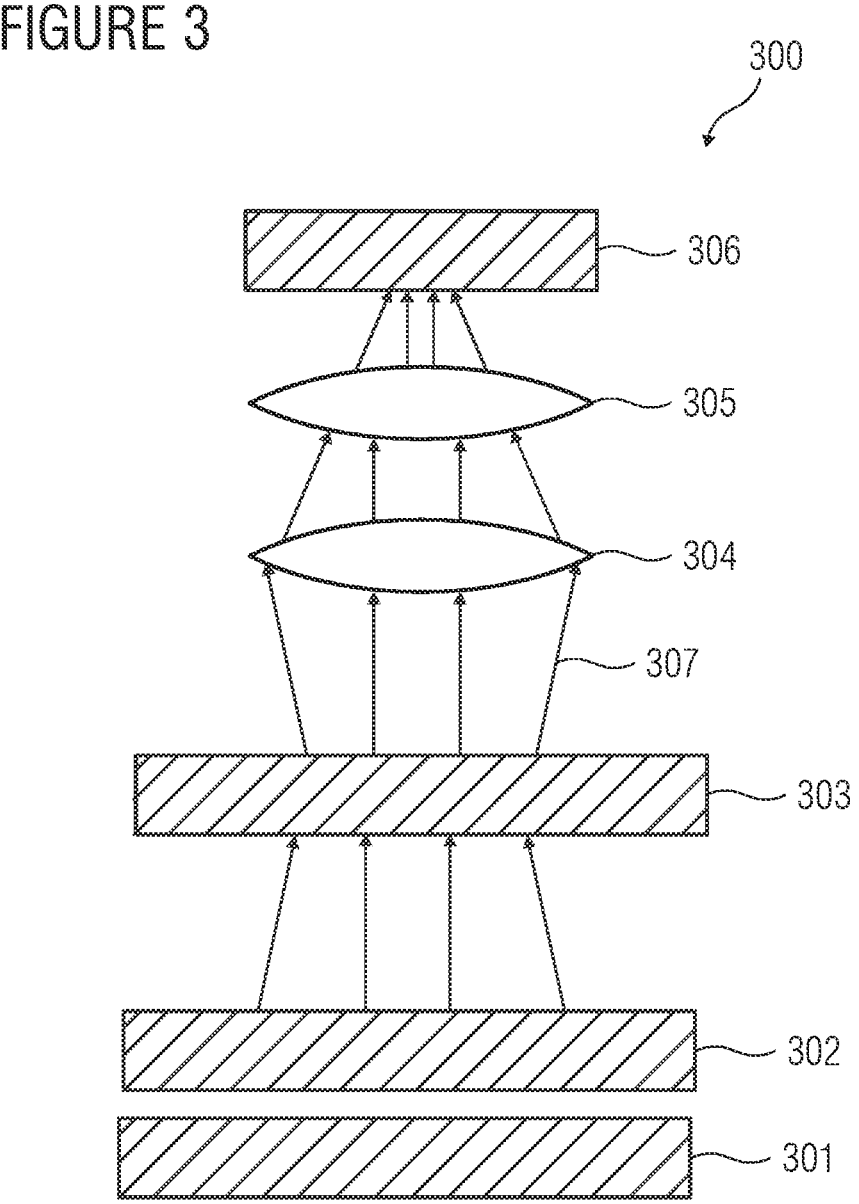
FIG. 3 illustrates an embodiment of an imaging module for generating a chromatically modified image of one or more components on a microscopic slide, according to an embodiment.

FIG. 3 illustrates an embodiment of an imaging module 300 for generating a chromatically modified image of one or more components on a microscopic slide. The imaging module 300 includes a light source 302 coupled to a processor 301. The light source 302 may be a multi-wavelength light source, i.e. capable of emitting light of varying wavelengths. In an embodiment, the light source 302 is configured to emit light of at least three different wavelength ranges. The wavelength ranges of the light source 302 may be, for example, between 400 nm and 420 nm; 440 nm and 480 nm; and 520 nm and 650 nm. In an embodiment, the light emitted 307 from the light source 302 passes through a microscopic slide 303 which includes one or more components to be imaged. The microscopic slide 303 may be, for example, a blood smear including a plurality of RBCs and WBCs. In an embodiment, the microscopic slide 303 may also be a pathology slide, for example, in case of a tissue biopsy. The imaging module 300 further includes an objective lens 304 to visualize and magnify the one or more components on the microscopic slide 303. The light 307 from the light source 302 radiates on to the microscopic slide 303. In an embodiment, the imaging module 300 may additionally include a tube lens 305. The tube lens 305 is used in microscopes to enable creation of real images from intermediate images placed at infinity. Therefore, tube lens 305 enable visualization of infinity corrected images. The imaging module 300 may also include an imaging capturing module 306. The image capturing module 306 may include imaging lenses and an imaging sensor, configured to capture an image of the illuminated microscopic slide 303. The imaging sensor may be, for example a charge-coupled device (CCD) or a complementary metal oxide semiconductor (CMOS). In an embodiment, the image capturing module 306 is also configured to transfer the captured image to the server 101 for further processing. In another embodiment, the image capturing module 306 is an exemplary embodiment of the input unit 204 in FIG. 2. In an embodiment, the imaging module 300 is a Fourier ptychography microscope. Fourier ptychography is a computational imaging technique where phase information associated with the one or more components on the microscopic slide 303 can be computationally derived. Phase information is a representation of refractive index changes observed when light 307 passes through the one or more components on the microscopic slide 303. Phase information of the one or more components can be used to differentiate areas of enhanced density or refractive index on the slide 303, such as nuclei of WBCs. Red blood cells (RBCs) and WBCs have unique phase profiles owing to the morphological differences between the cells. Such differences in phase information can be used to identify cell features such as nuclei of WBCs. In an embodiment, the Fourier ptychography microscope 300 may also be used to obtain chemical composition and morphological characteristics of the one or more components on the microscopic slide 303, simultaneously. Such chemical composition may be, for example, hemoglobin. Such chemical composition and morphological characteristics may be derived, for example, based on phase value associated with the one or more components present on the microscopic slide 303. In an embodiment, the morphological characteristics include morphological dimensions such as height and thickness of the cells. Morphological characteristics may also include morphological classification associated with the one or more components. In pathological slides, morphological characteristics may include determination of whether one or more cells are malignant or benign.

Figure 4:
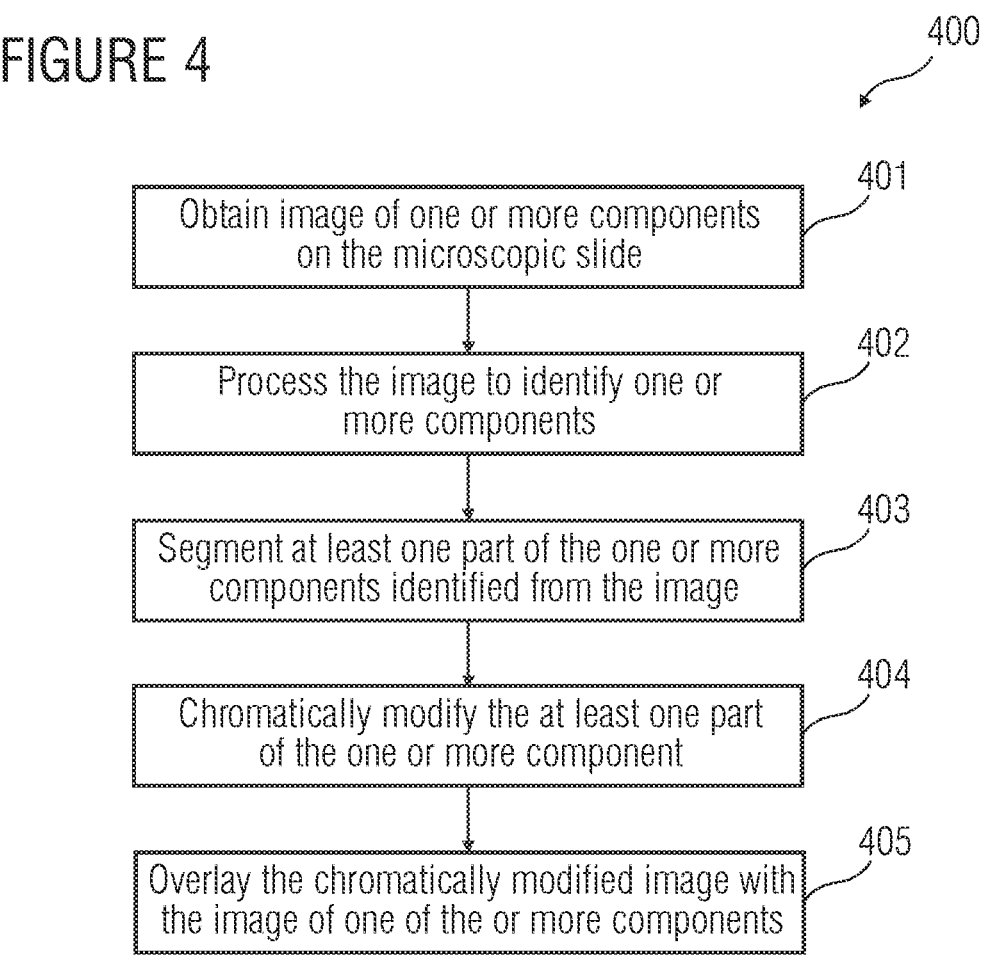
FIG. 4 illustrates a flowchart of a method generating a chromatically modified image of one or more components on a microscopic slide, according to an embodiment.

FIG. 4 illustrates a flowchart of an embodiment of a method 400 of generating a chromatically modified image of one or more components on a microscopic slide. At step 401, one or more images of one or more components on the microscopic slide is obtained. Such one or more images may be obtained from the imaging module 300. Such imaging module 300 may be, for example, a Fourier ptychography microscope. Traditional microscopic images captured by cameras may include only amplitude information. However, in Fourier ptychography microscopy, phase information can be derived computationally from one or more images of the same one or more components on the microscopic slide, illuminated at varying illumination angles. Such computational derivation of phase information may be performed using Gerchberg-Saxton algorithm. The phase image obtained from the algorithm enables calculation of key clinical hematological parameters such as hemoglobin concentration and mean corpuscular volume from cell thickness/height. A relationship between phase shift ($\Delta\phi$), concentration (C) and height (h) with a spatial dependence in a two-dimensional (x, y) plane is depicted below:

$$\Delta\phi(x,y;\lambda)=k_0[\beta(\lambda)C(x,y)+\Delta n_{ws}(\lambda)]h(x,y)$$

where $\lambda$ is wavelength of light, $\Delta n_{ws}$ is refractive index difference between water and surrounding media, and $\beta$ is the rate of change (mg/l) of the refractive index versus protein concentration. Fourier ptychography provides several unique technical advantages over traditional microscopy. Fourier ptychography enables a wide field of view with high resolution using a low magnification/resolution lens or objective lens. The hardware components of Fourier ptychography microscope are simple and mainly require an illumination source which can illuminate at multiple angles. Additionally, Fourier ptychography enables obtaining phase images at multiple wavelengths computationally using image reconstruction algorithms such as Gerchberg-Saxton algorithm. The phase difference between RBCs and WBCs based on the cell constituents and size may be exploited to generate a chromatically modified image of the one or more components on the microscopic slide. In an embodiment, the image of the one or more components on the microscopic slide may be obtained using the image capturing module 306 of the imaging module 300.

The method 400 further includes a step 402 of processing the image to identify one or more components on the microscopic slide. Processing of the image enables differentiating between the one or more components on the microscopic slide. In an embodiment, such identification of one or more components in the image may be performed by application of one or more thresholds to the obtained image. The method steps associated with processing the image are elaborated in detail in FIG. 5. At step 403 of the method 400, at least one part of the one or more components identified from the image are segmented. Such at least one part of the one or more components may be, for example, of clinical relevance. Such at least one part of the one or more components may include, for example, nuclei of the WBCs. The shape of the nuclei in WBCs enables identification of different types of WBCs. Therefore, segmentation of such nuclei for further processing may be essential. In an embodiment, segmentation of such at least one part of the one or more components on the microscopic slide may be performed using methods well known to a person skilled in the art. The method 400 further includes a step 404 of chromatically modifying the at least one part of the one or more components that is segmented at step 403. Chromatic modification of the at least one part enables efficient identification of such at least one part amidst the one or more components on the microscopic slide. Chromatic modification enables creation of an effect of staining that is clinically performed by staining experts to visualize one or more components on a microscopic slide. In the present embodiment, the chromatic modification of the at least one part of the one or more components on the microscopic slide is performed computationally and therefore, the requirement of manual staining of such microscopic slide is avoided. The method steps elaborating the process of chromatic modification of the at least one part of the one or more components is provided in FIG. 6.

At step 405, the chromatically modified image of the at least one part of the one or more components on the microscopic slide is overlaid with the image obtained from the imaging module 300 at step 401. The chromatically modified image is overlaid such that the chromatically modified at least one part of the one or more components is positioned exactly over the unmodified at least one part of the one or more components in the image obtained at step 401. In an embodiment, the overlaying of images may be performed, for example, using coordinate mapping and/or pixel mapping of the images. Advantageously, overlaying the chromatically modified at least one part of the one or more components enables generation of a chromatically modified image of the one or more components on the microscopic slide. Therefore, chromatic modification of the at least part of the one or more components enables creation of a staining effect on the one or more components on the microscopic slide. Therefore, manual effort of staining the slides is avoided. This enables efficient and uniform staining of the components on the microscopic slide, thereby making the process of analyzing such microscopic slides simpler and faster. Additionally, manual effort in staining the microscopic slides is reduced and variability in stains is eliminated. Furthermore, the method is cost effective in that the laboratory infrastructure and man power is efficiently managed.

Figure 5:
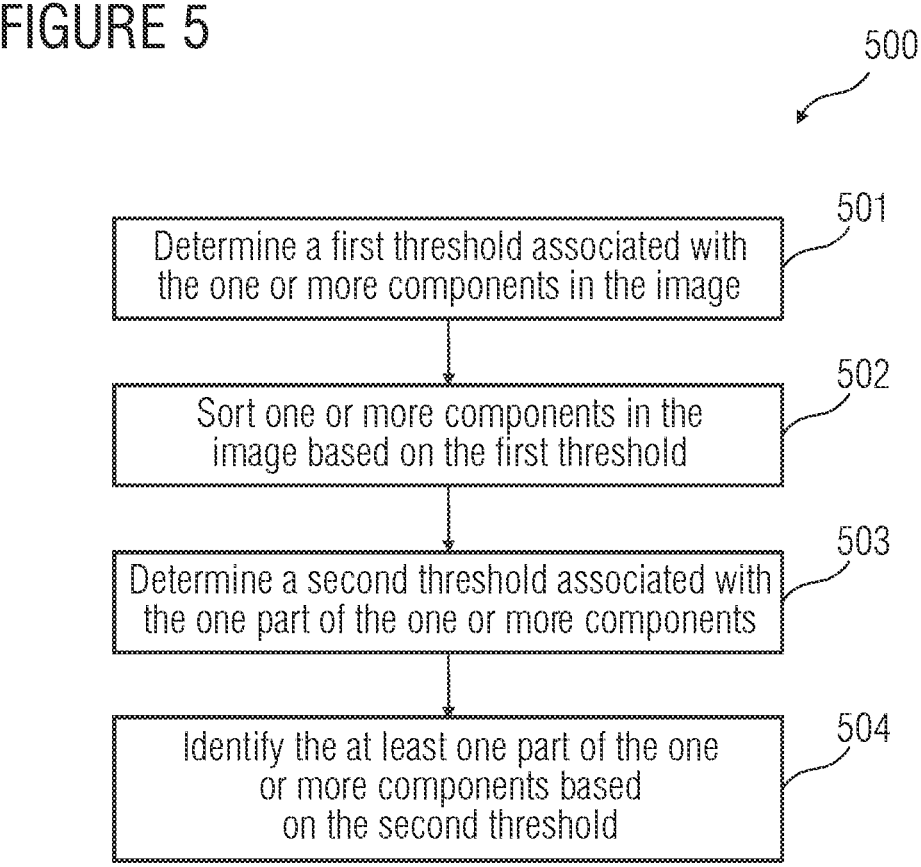
FIG. 5 illustrates a flowchart of a method of processing the image to identify the one or more components, according to an embodiment.

FIG. 5 illustrates a flowchart of a method 500 of processing the obtained image to identify one or more components. At step 501, a first threshold associated with the one or more components in the image is identified. The first threshold may be, for example, size of the one or more components in the image. WBCs are bigger in size in comparison to RBCs. Therefore, the first threshold is set such that the WBCs are separated out from the RBCs efficiently. The size of the one or more components may be determined, for example, based on the area or circumference of the components in the image. Such determination may be based on the pixel intensity values associated with cellular boundaries of the one or more components in the image. At step 502, the one or more components in the image are sorted based on the first threshold. Sorting of the one or more components in the image enables separation of the one or more components based on the size of the one or more components. At step 503, a second threshold associated with the at least one part of the one or more components is identified. Such second threshold may be, for example, a contrast value associated with the at least one part of the one or more components. Alternatively, phase information associated with the at least one part of the one or more components may be used as a second threshold. In an embodiment, if the at least one part of the one or more components is a nuclei of the WBCs, such nuclei may have a higher contrast value in comparison to surrounding media. Therefore, the second threshold enables efficient identification of the at least one part of the one or more components in the image. At step 504, the at least one part of the one or more components in the image is identified based on the second threshold. Such identification is performed based on the contrast values associated with the at least one part of the one or more components in the image. Advantageously, the method enables accurate identification of components in the image which are of clinical relevance. The method further enables uniform chromatic modification of the identified components in the image.

Figure 6:
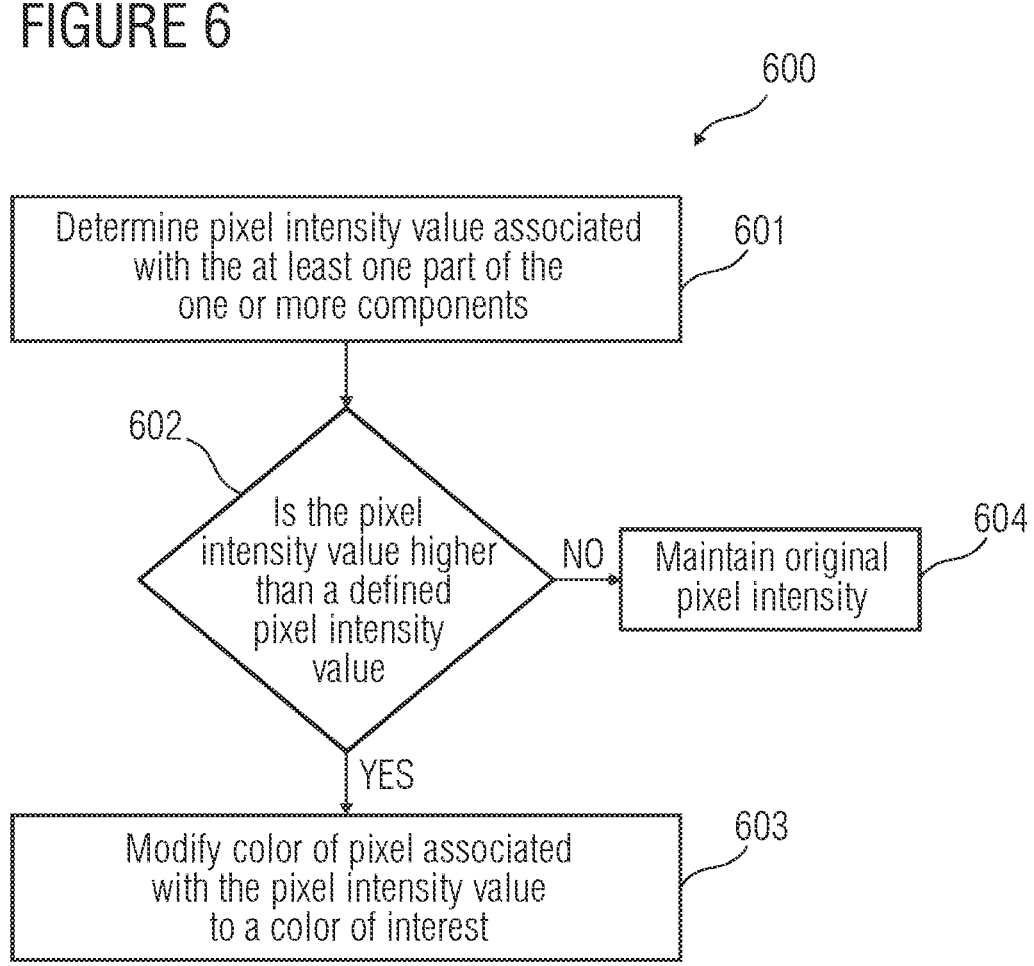
FIG. 6 illustrates a flowchart of a method of chromatically modifying at least one of the one or more components in the image, according to an embodiment.

FIG. 6 illustrates a flowchart of a method 600 of chromatically modifying the at least one part of the one or more components in the image, according to an embodiment. At step 601, pixel intensity values associated with the segmented one or more components is identified. In an embodiment, the segmented one or more components may have an associated contrast value. Such contrast value may be dependent on the density of such one or more components or of the parts of the one or more components. Therefore, the nucleus of a WBC may have a higher associated contrast value in comparison to other constituents of the WBC. Therefore, the pixel intensity value associated with such nucleus is greater in comparison to the other constituents of the WBC. At step 602, a determination is made if the pixel intensity value associated with the segmented one or more components is higher than a defined pixel intensity value. Such defined pixel intensity value may be a threshold based on which at least one part of the segmented one or more components is identified. Such at least one part of the segmented one or more components may be the nucleus of the WBC. At step 603, if the pixel intensity value is greater than the defined pixel intensity value, the colour associated with the corresponding pixel is modified to a colour of interest. This enables chromatic modification of the one or more components in the image. Chromatic modification enables efficient determination of the one or more components of clinical relevance. If the pixel intensity value is lesser than the defined pixel intensity value, the original pixel intensity value is maintained at step 604. In an embodiment, the colour for chromatic modification may be chosen such that the colour resembles a clinically stained microscopic slide. In a further embodiment, image processing algorithms well known in the art may be used to generate a chromatically modified image that is photorealistic and more emphasized in colour scheme. Additionally, amplitude information may also be used to make the chromatically modified image more realistic.

Figure 7:
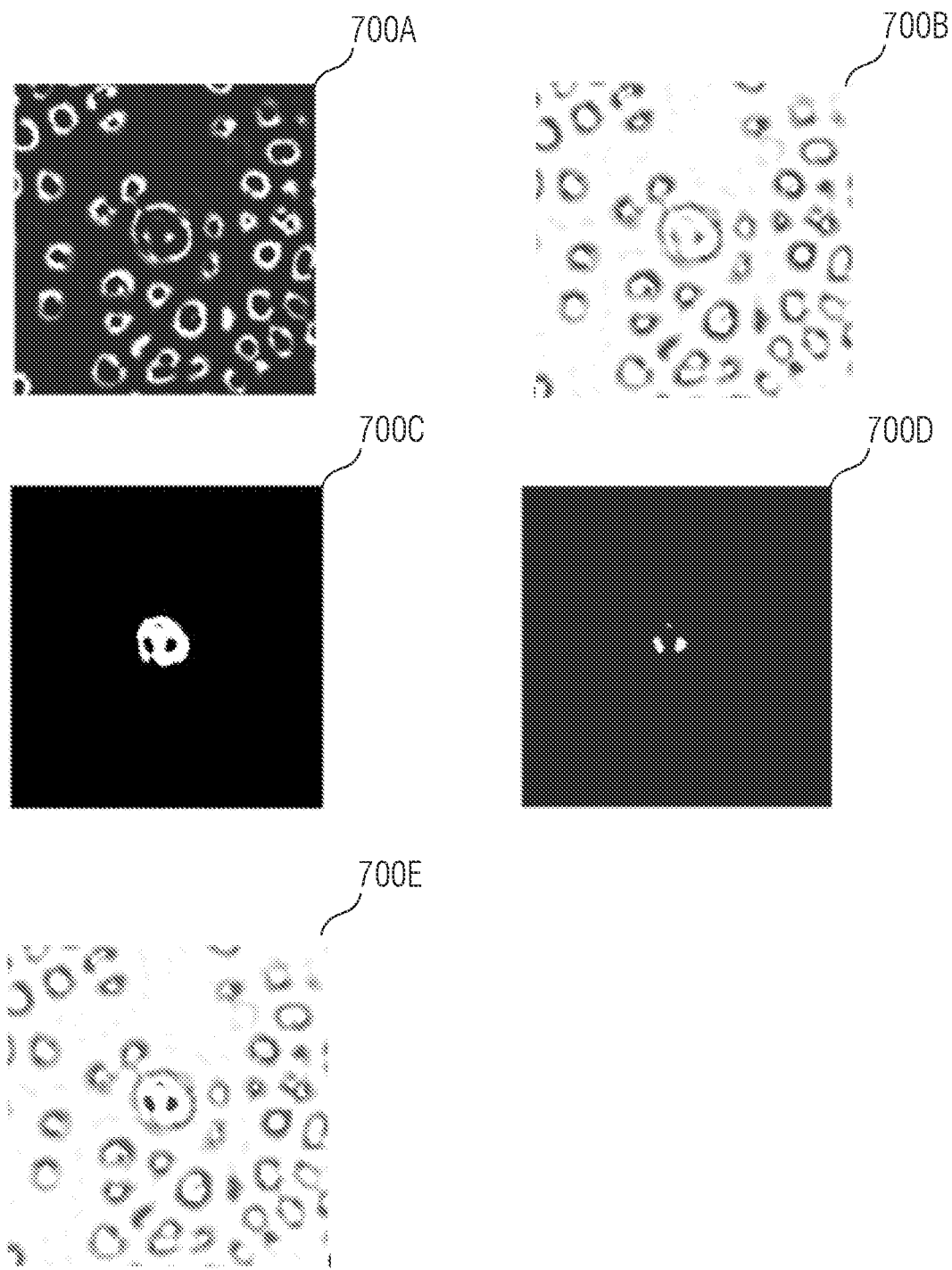
FIG. 7 illustrates an embodiment of chromatically modified image of one or more components on a microscopic slide.

FIG. 7 illustrates an embodiment of chromatically modified image of one or more components on a microscopic slide. The imaged microscopic slide is a blood smear slide, including a plurality of RBCs and WBCs. Image 700A depicts a phase reconstruction of the blood smear slide using Fourier ptychography microscope 300. Image 700B depicts processing of the phase image of the one or more components based on the first threshold, i.e. size of the cells. Image 700C depicts segmentation of the WBC based on the first threshold and the second threshold, i.e. contrast value. Image 700D depicts chromatic modification of the nucleus of the WBC based on the pixel intensity value associated with the nucleus. Image 700E depicts a chromatically modified image of the one or more components on the microscopic slide. Such chromatically modified image is created by overlaying the chromatically modified segmented image 700D with the original image 700B. The image 700E clearly depicts the nucleus of the WBC for further clinical processing.

The above invention may be used for staining of pathological slides, cells, cellular components, intracellular and extracellular components in several microscopy images such as smears, cytology/cellular imaging and tissue and digital pathology. Fourier ptychography is a computational imaging method where the phase information can be derived computationally. Phase images obtained from Fourier ptychography microscope have higher contrast values as compared to other phase enhancement techniques such as phase contrast microscopy or differential interference contrast microscopy. Therefore, the proposed invention is an efficient and simple phase imaging technique for stain-free slide microscopy. Additionally, the invention is also cost effective and may not include any movable parts. With image processing, chromatically modified images may look similar to the stained microscope images that a clinical pathologist may generate using manual staining process.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

What is claimed is:

1. A method of generating a chromatically modified image of one or more components in a sample on a microscopic slide, the method comprising:
    obtaining the image of the sample containing one or more components on the microscopic slide wherein the sample and the one or more components are stain-free;
    processing the image to identify the one or more components;
    segmenting at least one part of the one or more components identified in the image;
    chromatically modifying the image containing at least one part of the one or more components; and
    generating a chromatically modified image of the one or more components.

2. The method according to claim 1, wherein processing the image to identify the one or more components in a sample comprises:
    determining a first threshold associated with the one or more components in the image;
    sorting the one or more components in the image based on the first threshold;
    determining a second threshold associated with the at least one part of the one or more components; and
    identifying the at least one part of the one or more components in the image based on the second threshold.

3. The method according to claim 2, wherein the first threshold is a size of the one or more components on the microscopic slide and the second threshold is a contrast value associated with the one or more components on the microscopic slide.

4. The method according to claim 1, further comprising deriving clinical information associated with the one or more components in the sample on the microscopic slide, wherein the clinical information associated with the one or more components includes morphological characteristics and chemical composition associated with the one or more components.

5. The method according to claim 1, wherein chromatically modifying the at least one part of the one or more components in the image comprises:
    identifying a pixel intensity value associated with the at least one part of the one or more components in the image;
    if the pixel intensity value is higher than a defined pixel intensity value, mapping such pixel intensity value associated with the at least one part of the one or more components to a color; and
    modifying a color associated with a pixel corresponding to such pixel intensity value to the mapped color.

6. The method according to claim 5, wherein the image is constructed using phase information associated with the one or more components on the microscopic slide.

7. The method according to claim 1, wherein generating the chromatically modified image of the one or more components further comprises overlaying the segmented at least one part of the one or more components with the image of the one or more components on the microscopic slide.

8. The method according to claim 1, wherein the image of the one or more components on the microscopic slide is obtained using Fourier ptychography microscope.

9. The method according to claim 4, wherein clinical information is derived based on phase value associated with the one or more components in the sample on the microscopic slide.

10. A system for generating a chromatically modified image of one or more components in a sample on a microscopic slide the system comprising:
an imaging microscope;
one or more processing units;
a database coupled to the processing units;
a memory coupled to the processing units, the memory comprising an image processor configured for:
obtaining the image of the sample containing one or more components on the microscopic slide wherein the sample and the one or more components are stain-free;
processing the image to identify the one or more components;
segmenting at least one part of the one or more components identified in the image;
chromatically modifying the image containing at least one part of the one or more components; and
generating a chromatically modified image of the one or more components.

11. The system according to claim 10, wherein in processing the image to identify the one or more components, the image processor is configured to:
determine a first threshold associated with the one or more components in the image;
sort the one or more components in the image based on the first threshold;
determine a second threshold associated with the at least one part of the one or more components; and
identify the at least one part of the one or more components in the image based on the second threshold.

12. The system according to claim 10, wherein in chromatically modifying the at least one of the one or more components in the image, the imaging processor is configured to:
identify a pixel intensity value associated with the at least one part of the one or more components in the image; and
if the pixel intensity value is higher than a defined pixel intensity value, map such pixel intensity value associated with the at least one part of the one or more components to a color.

13. The system according to claim 10, wherein in generating the chromatically modified image of the one or more components the image processor is further configured to overlay the segmented at least one part of the one or more components with the image of the one or more components on the microscopic slide.

14. The system according to claim 10, wherein the imaging microscope is a Fourier ptychography microscope.

15. The system according to claim 10, wherein the image of the one or more components is constructed using Fourier ptychography microscope using phase information associated with such one or more components on the microscopic slide.

16. The system of claim 10, wherein the imaging microscope comprises:
a controllable light source capable of emitting light at plurality of discrete angles;
a tube lens;
one or more objective lens; and
an imaging capturing module.

17. A non-transitory computer-readable storage medium having machine-readable instructions stored therein, that when executed by a server, cause the server to perform the method steps comprising:
obtaining an image of the sample containing one or more components on the microscopic slide wherein the sample and the one or more components are stain-free;
processing the image to identify the one or more components;
segmenting at least one of the one or more components identified in the image;
chromatically modifying the image containing at least one of the one or more components; and
generating a chromatically modified image of the one or more components.

* * * * *